United States Patent [19]

Lacroix

[11] 4,044,145
[45] Aug. 23, 1977

[54] FUNGICIDAL COMPOSITIONS

[75] Inventor: Laurent Lacroix, Villers St-Fargeau, France

[73] Assignee: Rhone-Poulenc Industries, Paris, France

[21] Appl. No.: 595,605

[22] Filed: July 14, 1975

[30] Foreign Application Priority Data

July 15, 1974 France .................................. 74.24511
June 4, 1975 France .................................. 75.17425

[51] Int. Cl.$^2$ .......................... A01N 9/02; A01N 9/12; A01N 9/22
[52] U.S. Cl. .............................. 424/273 R; 424/245; 424/258; 424/270; 424/274; 424/300; 424/328
[58] Field of Search ................................ 424/273, 300

[56] References Cited

FOREIGN PATENT DOCUMENTS

| 1,190,614 | 5/1970 | United Kingdom |
| 1,191,406 | 5/1970 | United Kingdom |
| 1,193,462 | 6/1970 | United Kingdom |
| 1,312,536 | 4/1973 | United Kingdom |
| 1,312,743 | 4/1973 | United Kingdom |

Primary Examiner—Allen J. Robinson
Attorney, Agent, or Firm—Stevens, Davis, Miller & Mosher

[57] ABSTRACT

Fungicidal compositions comprising 1-isopropylcarbamoyl-3-(3,5-dichlorophenyl)hydantoin and at least one fungicide selected from 2-methoxycarbonylaminobenzimidazole, 1-butylcarbamoyl-2-methoxycarbonylaminobenzimidazole, 1,2-bis-(3-methoxycarbonylthioureido)-benzene, 2-methoxycarbonylimino-3-(2-aminophenyl)-thiazolidin-4-one, tetramethylthiuram disulphide, N-trichloromethylthiophthalimide and copper hydroxyquinolinate, are especially useful for the disinfection of seeds.

7 Claims, No Drawings

FUNGICIDAL COMPOSITIONS

THIS INVENTION relates to new fungicidal compositions which can be used in particular for the disinfection of seeds, and more generally for combating phytopathogenic fungi.

In the specification of British Pat. No. 1,312,536 granted to Rhone-Poulenc S.A. on an application filed 6th Oct. 1971 there are described and claimed hydantoin derivatives of the general formula:

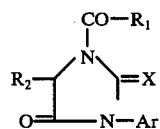

(wherein Ar represents a phenyl radical or a phenyl radical carrying one to five substituents, which may be the same or different, selected from halogen atoms (preferably chlorine), alkyl and alkoxy radicals containing 1 to 4 carbon atoms and the trifluoromethyl radical, $R_1$ represents an alkoxy radical containing 1 to 4 carbon atoms or a grouping —$NR_3R_4$, in which $R_3$ and $R_4$ are the same or different and each represents a hydrogen atom, an alkyl radical containing 1 to 4 carbon atoms or an alkenyl radical containing 2 to 4 carbon atoms, $R_2$ represents a hydrogen atom or an alkyl radical containing 1 to 4 carbon atoms, and X represents an oxygen or sulphur atom), which possess fungicial properties. They are particularly useful for the treatment of vines, strawberry plants, fruit trees (e.g. peach, apricot and cherry trees) and market gardening produce (e.g. vegetables for salads) to control fungal infections.

A hydantoin derivative of very particular interest is that of the depicted general formula wherein Ar represents the 3,5-dichlorophenyl radical, $R_1$ represents a grouping —$NR_3R_4$ in which $R_3$ represents a hydrogen atom and $R_4$ represents the isopropyl radical, and X represents an oxygen atom, that is to say 1-isopropylcarbamoyl-3-(3,5-dichlorophenyl)hydantoin.

It has now unexpectedly been found after further research and experimentation, and it is this which forms the subject of the present invention, that combination of 1-isopropylcarbamoyl-3-(3,5-dichlorophenyl)hydantoin with at least one other fungicide selected from 2-methoxycarbonylamino-benzimidazole (carbendazime), 1-butylcarbamoyl-2-methoxycarbonylaminobenzimidazole (benomyl), 1,2-bis-(3-methoxycarbonylthioureido)benzene (methylthiophanate), 2-methoxycarbonylimino-3-(2-aminophenyl)thiazolidin-4-one, tetramethylthiuram disulphide (thiram), N-trichloromethylthiophthalimide (folpet) and copper hydroxyquinolinate, enhances the effect of the other fungicide. The said combinations of fungicides are particularly useful for the disinfection of seeds.

The fungicidal properties of thiram, folpet and copper hydroxyquinolinate are well-known; those of carbendazime, benomyl, methylthiophanate and 2-methoxycarbonylimino-3-(2-aminophenyl)thiazolidin-4-one are described in inter alia the specifications of British Pat. Nos. 1,190,614 and 1,193,462 (both granted to E. I. Du Pont de Nemours and Company), 1,191,406 (Nippon Soda Company Limited) and 1,312,743 (Rhone-Poulenc S.A.) respectively.

The aforesaid combinations which contain 1-isopropylcarbamoyl-3-(3,5-dichlorophenyl)hydantoin exhibit a remarkable activity against *Fusarium oxysporum* on melons, *Fusarium nivale* and *Septora nodorum* on wheat, *Pyrenophora avenae* on oats, and *Fusarium culmorum* and *Pyrenophora graminae* on barley. They are also active against wheat rust (*Puccinia glumarum*), bean anthracnose (*Collectotrichum lindemuthianum*) and cucumber mildew (*Erysiphae cichloracearum*).

1-Isopropylcarbamoyl-3-(3,5-dichlorophenyl)-hydantoin advantageously complements the spectrum of activity of the aforementioned antifungal agents usually employed. This complementary action is the more marked where it is necessary to combat not only one parasite but a group of parasites. The combinations are also particularly effective for the treatment of seeds or barley infested by *Helminthosporium gramineum* and *Fusarium culmorum*, grass infested by *Sclerotinia homeocarpa*, *Fusarium roseum* and *Helminthosporium sp.*, and carrots infested by Pythium sp., *Rhizoctonia violacea* and *Alternaria dauci*.

The activity of the combinations according to the invention can be demonstrated as follows:

The products to be studied, individually or in combination, are ground in a mortar and then incorporated in an inert carrier such as talc, so as to set up a range of concentrations.

The contaminated seeds are coated with the formulations of the products by means of a rotary mixer.

The seeds for comparison purposes are coated with the inert carrier.

The contaminated seeds are placed in Petri dishes (diameter 150 mm.), on the surface of a nutrient medium (70 cm³ of medium per dish) which has been sterilised for 15 minutes at 120° C.

Each dish contains a hundred seeds and two dishes are used for each concentration.

With their covers on, these dishes are kept at 25° + 1° C. for 5 days.

On the fifth day of the test, the seeds which have given rise to a colony of the parasite are counted in each dish. For each product the concentration, expressed in mg. of active product per gram of seeds, which ensures 95 to 100% disinfection of the seeds, is determined. The percentage activity of the active products at each particular concentration given in the following Tables is the percentage of the seeds which give rise to no colony of the parasite.

TABLE No. 1

| Action on *Fusarium oxysporum* of melons | | | | |
|---|---|---|---|---|
| Products and combinations studied (the combinations are 50:50 by weight) | Percentage activity at the following concentrations (in mg. of product per g. of seed) | | | |
| | 2.0 | 1.0 | 0.5 | 0.25 |
| 1-Isopropylcarbamoyl-3-(3,5-dichlorophenyl)hydantoin | 26 | 7 | 0 | 0 |
| Carbendazime | 80 | 66 | 51 | 30 |
| Benomyl | 85 | 72 | 54 | 38 |
| 2-Methoxycarbonylimino-3-(2-aminophenyl)-thiazolidin-4-one | 74 | 60 | 44 | 21 |
| 1-Isopropylcarbamoyl-3-(3,5-dichlorophenyl)hydantoin + Carbendazime | 100 | 100 | 99 | 87 |
| 1-Isopropylcarbamoyl-3-(3,5-dichlorophenyl)hydantoin + Benomyl | 100 | 100 | 97 | 80 |
| 1-Isopropylcarbamoyl-3-(3,5-dichlorophenyl)hydantoin + 2-Methoxycarbonylimino-3-(2-aminophenyl)-thiazolidin-4-one | 100 | 100 | 80 | 62 |
| Contaminated untreated reference | | | | |

TABLE No. 1-continued

Action on *Fusarium oxysporum* of melons

| Products and combinations studied (the combinations are 50:50 by weight) | Percentage activity at the following concentrations (in mg. of product per g. of seed) | | | |
|---|---|---|---|---|
| | 2.0 | 1.0 | 0.5 | 0.25 |
| samples | 0 | | | |

TABLE No. 2

Action on *Fusarium nivale* of wheat

| Products and combinations studied (the combinations are 50:50 by weight) | Percentage activity at the following concentrations (in mg. of product per g. of seed) | | | |
|---|---|---|---|---|
| | 2.0 | 1.0 | 0.5 | 0.25 |
| 1-Isopropylcarbamoyl-3-(3,5-dichlorophenyl)hydantoin | 17 | 3 | 0 | 0 |
| Carbendazime | 86 | 73 | 48 | 26 |
| Benomyl | 84 | 70 | 50 | 30 |
| 2-Methoxycarbonylimino-3-(2-aminophenyl)-thiazolidin-4-one | 78 | 65 | 37 | 24 |
| 1-Isopropylcarbamoyl-3-(3,5-dichlorophenyl)hydantoin + Carbendazime | 100 | 100 | 99 | 88 |
| 1-Isopropylcarbamoyl-3-(3,5-dichlorophenyl)hydantoin + Benomyl | 100 | 100 | 100 | 75 |
| 1-Isopropylcarbamoyl-3-(3,5-dichlorophenyl)hydantoin + 2-Methoxycarbonylimino-3-(2-aminophenyl)-thiazolidin-4-one | 100 | 100 | 89 | 61 |
| Contaminated untreated reference samples | 0 | | | |

TABLE No. 3

Action on *Septoria nodorum* of wheat

| Products and combinations studied (the combinations are 50:50 by weight) | Percentage activity at the following concentrations (in mg. of product per g. of seed) | | | |
|---|---|---|---|---|
| | 2.0 | 1.0 | 0.5 | 0.25 |
| 1-Isopropylcarbamoyl-3-(3,5-dichlorophenyl)hydantoin | 63 | 48 | 17 | 0 |
| Carbendazime | 91 | 84 | 68 | 43 |
| Benomyl | 92 | 80 | 70 | 44 |
| Methylthiophanate | 80 | 76 | 57 | 38 |
| 2-Methoxycarbonylimino-3-(2-aminophenyl)-thiazolidin-4-one | 88 | 76 | 60 | 39 |
| 1-Isopropylcarbamoyl-3-(3,5-dichlorophenyl)hydantoin + Carbendazime | 100 | 100 | 98 | 91 |
| 1-Isopropylcarbamoyl-3-(3,5-dichlorophenyl)hydantoin + Benomyl | 100 | 99 | 99 | 93 |
| 1-Isopropylcarbamoyl-3-(3,5-dichlorophenyl)hydantoin + Methylthiophanate | 100 | 98 | 94 | 88 |
| 1-Isopropylcarbamoyl-3-(3,5-dichlorophenyl)hydantoin + 2-Methoxycarbonylimino-3-(2-aminophenyl)-thiazolidin-4-one | 100 | 99 | 98 | 90 |
| Contaminated untreated reference samples | 0 | | | |

TABLE No. 4

Action on *Pyrenophora avenae* of oats

| Products and combinations studied (the combinations are 50:50 by weight) | percentage activity at the following concentrations (in mg. of product per g. of seed) | | | |
|---|---|---|---|---|
| | 2.0 | 1.0 | 0.5 | 0.25 |
| 1-Isopropylcarbamoyl-3-(3,5-dichlorophenyl)hydantoin | 96 | 93 | 84 | 68 |
| Carbendazime | 14 | 0 | 0 | 0 |
| Benomyl | 10 | 0 | 0 | 0 |
| Methylthiophanate | 0 | 0 | 0 | 0 |
| 2-Methoxycarbonylimino-3-(2-aminophenyl)-thiazolidin-4-one | 6 | 0 | 0 | 0 |
| 1-Isopropylcarbamoyl-3-(3,5-dichlorophenyl)hydantoin + Carbendazime | 100 | 99 | 91 | 86 |
| 1-Isopropylcarbamoyl-3-(3,5-dichlorophenyl)hydantoin + Benomyl | 100 | 100 | 94 | 90 |
| 1-Isopropylcarbamoyl-3-(3,5-dichlorophenyl)hydantoin + Methylthiophanate | 94 | 98 | 87 | 87 |
| 1-Isopropylcarbamoyl-3-(3,5-dichlorophenyl)hydantoin + 2-Methoxycarbonylimino-3-(2-aminophenyl)-thiazolidin-4-one | 99 | 98 | 86 | 79 |
| Contaminated untreated reference samples | 0 | | | |

TABLE No. 5

Action on *Pyrenophora graminae* of barley

| Products and combinations studied (the combinations are 50:50 by weight) | Percentage activity at the following concentrations (in mg. of product per g. of seed) | | | |
|---|---|---|---|---|
| | 2.0 | 1.0 | 0.5 | 0.25 |
| 1-Isopropylcarbamoyl-3-(3,5-dichlorophenyl)hydantoin | 94 | 97 | 80 | 57 |
| Carbendazime | 3 | 0 | 0 | 0 |
| Benomyl | 0 | 0 | 0 | 0 |
| Methylthiophanate | 0 | 0 | 0 | 0 |
| 2-Methoxycarbonylimino-3-(2-aminophenyl)-thiazolidin-4-one | 0 | 0 | 0 | 0 |
| 1-Isopropylcarbamoyl-3-(3,5-dichlorophenyl)hydantoin + Carbendazime | 99 | 99 | 95 | 80 |
| 1-Isopropylcarbamoyl-3-(3,5-dichlorophenyl)hydantoin + Benomyl | 99 | 100 | 99 | 77 |
| 1-Isopropylcarbamoyl-3-(3,5-dichlorophenyl)hydantoin + Methylthiophanate | 99 | 99 | 91 | 69 |
| 1-Isopropylcarbamoyl-3-(3,5-dichlorophenyl)hydantoin + 2-Methoxycarbonylimino-3-(2-aminophenyl)-thiazolidin-4-one | 98 | 99 | 90 | 70 |
| Contaminated untreated reference samples | 0 | | | |

TABLE No. 6

Experiment on barley seed

Combination of parasites: *Helminthosporium gramineum* and *Fusarium culmorum*

| Products and combinations studied (the combinations are 50:50 by weight) | Percentage activity at the following concentrations (in mg. of product per g. of seed) | | | |
|---|---|---|---|---|
| | 2.0 | 1.0 | 0.5 | 0.25 |
| Thiram | 98 | 68 | 39 | 31 |
| Folpet | 86 | 83 | 62 | 59 |
| Copper hydroxyquinolinate | 91 | 77 | 58 | 26 |
| 1-Isopropylcarbamoyl-3-(3,5-dichlorophenyl)hydantoin | | | | |

TABLE No. 6-continued

Experiment on barley seed

Combination of parasites: *Helminthosporium gramineum* and *Fusarium culmorum*

| Products and combinations studied (the combinations are 50:50 by weight) | Percentage activity at the following concentrations (in mg. of product per g. of seed) | | | |
|---|---|---|---|---|
| | 2.0 | 1.0 | 0.5 | 0.25 |
| + Thiram | 99 | 87 | 48 | 32 |
| 1-Isopropylcarbamoyl-3-(3,5-dichlorophenyl)hydantoin + Folpet | 100 | 96 | 90 | 74 |
| 1-Isopropylcarbamoyl-3-(3,5-dichlorophenyl)hydantoin + Copper hydroxyquinolinate | 99 | 90 | 74 | 37 |

TABLE No. 7

Experiment on grass seed

Combination of parasites: *Fusarium roseum, Helminthosporium* sp. and *Sclerotinia homeocarpa*

| Products and combinations studied (the combinations are 50:50 by weight) | Percentage activity at the following concentrations (in mg. of product per g. of seed) | | | |
|---|---|---|---|---|
| | 2.0 | 1.0 | 0.5 | 0.25 |
| Thiram | 89 | 63 | 28 | 11 |
| Folpet | 90 | 74 | 47 | 24 |
| Copper hydroxyqinolinate | 58 | 44 | 19 | 0 |
| 1-Isopropylcarbamoyl-3-(3,5-dichlorophenyl)hydantoin + Thiram | 96 | 79 | 34 | 7 |
| 1-Isopropylcarbamoyl-3-(3,5-dichlorophenyl)hydantoin + Folpet | 100 | 91 | 60 | 38 |
| 1-Isopropylcarbamoyl-3-(3,5-dichlorophenyl)hydantoin + Copper hydroxyqinolinate | 88 | 66 | 31 | 9 |

TABLE No. 8

Experiment on carrot seed

Combination of parasites: *Pythium* sp., *Rhizoctonia violacea* and *Ahernaria dauci*

| Products and combinations studied (the combinations are 50:50 by weight) | Percentage activity at the following concentrations (in mg. of product per g. of seed) | | | |
|---|---|---|---|---|
| | 2.0 | 1.0 | 0.5 | 0.25 |
| Thiram | 62 | 48 | 12 | 0 |
| Folpet | 60 | 36 | 9 | 0 |
| Copper hydroxyquinolinate | 49 | 17 | 0 | 0 |
| 1-Isopropylcarbamoyl-3-(3,5-dichlorophenyl)hydantoin + Thiram | 83 | 67 | 34 | 8 |
| 1-Isopropylcarbamoyl-3-(3,5-dichlorophenyl)hydantoin + Folpet | 97 | 85 | 48 | 22 |
| 1-Isopropylcarbamoyl-3-(3,5-dichlorophenyl)hydantoin + Copper hydroxyquinolinate | 86 | 39 | 12 | 0 |

These results show that the activity of the products used in combination is markedly superior to that of the products considered individually.

The synergistic effect is apparent when the proportion of 1-isopropylcarbamoyl-3-(3,5-dichlorophenyl)-hydantoin in the combination is between 10% and 90% by weight; however, the maximum effect is obtained if this proportion is between 30% and 70%.

The results obtained are summarised in Table No. 9.

TABLE No. 9

| 1-Isopropylcarbamoyl-3-(3,5-dichlorophenyl)hydantoin Percentage | Carbendazine Percentage | Percentage activity at the concentrations shown below, which are expressed in mg. of total active material per g. of seed | | | | | |
|---|---|---|---|---|---|---|---|
| | | *Fusarium nivale* of wheat | | *Pyrenophora graminea* of barley | | *Pyrenophora graminea* and *Fusarium culmorum* of barley (combination of parasites) | |
| | | 1.0 | 0.5 | 1.0 | 0.5 | 1.0 | 0.5 |
| 100 | 0 | 6 | 0 | 98 | 82 | 1.5 | 0 |
| 90 | 10 | 11 | 2 | 99 | 90 | 11 | 4 |
| 80 | 20 | 33 | 18 | 100 | 94 | 88 | 23 |
| 70 | 30 | 91 | 76 | 100 | 99 | 96 | 76 |
| 60 | 40 | 99 | 85 | 100 | 100 | 97 | 85 |
| 50 | 50 | 99 | 99 | 100 | 95 | 100 | 95 |
| 40 | 60 | 97 | 99 | 96 | 78 | 99 | 98 |
| 30 | 70 | 97 | 94 | 84 | 61 | 93 | 92 |
| 20 | 80 | 98 | 90 | 64 | 30 | 91 | 83 |
| 10 | 90 | 93 | 77 | 21 | 0 | 86 | 50 |
| 0 | 100 | 84 | 53 | 0 | 0 | 0 | 0 |
| Untreated reference samples | | 0 | | | | | |

The present invention also includes within its scope fungicidal compositions comprising a combination of 1-isopropylcarbamoyl-3-(3,5-dichlorophenyl)hydantoin with carbendazime, benomyl, methylthiophanate, 2-methoxycarbonylimino-3(2-aminophenyl)-thiazolidin-4-one, thiram, folpet or copper hydroxyquinolinate, in association with one or more diluents or adjuvants which are inert and compatible therewith and suitable for use in agricultural fungicidal compositions. In these compositions, the content of active material is preferably between 0.005% and 80% by weight, the active material consisting of a combination according to the invention in which the proportion of 1-isopropylcarbamoyl-3-(3,5-dichlorophenyl)-hydantoin is generally between 10% and 90%, and preferably between 30% and 70%, by weight of the combination.

The compositions may be solid if there is employed a powdered solid compatible diluent such as talc, calcined magnesia, kieselguhr, tricalcium phosphate, powdered cork, adsorbent charcoal, or a clay such as kaolin or bentonite. These solid compositions are preferably prepared by grinding the active material with the solid diluent, or by impregnating the solid diluent with a solution of the active material in a volatile solvent, evaporating the solvent, and if necessary grinding the product so as to obtain a powder.

Instead of a solid diluent, there may be used a liquid in which the active material is dissolved or dispersed, e.g. water. The compositions may thus take the form of suspensions, emulsions or solutions in organic or aqueous-organic media, for example aromatic hydrocarbons such as toluene or xylene, mineral, animal or vegetable oils, anisole, cyclohexanone or acetophenone, or mixtures of these diluents. The compositions in the form of suspensions, emulsions or solutions may contain wetting, dispersing or emulsifying agents of the ionic or non-ionic type, for example sulphoricinoleates, quaternary ammonium derivatives or products based on condensates of ethylene oxide, such as the condensates of ethylene oxide with octylphenol, or fatty acid esters of anhydrosorbitols which have been rendered soluble by etherification of the free hydroxy groups by condensation with ethylene oxide. It is preferably to use agents of the non-ionic type because they are not sensitive to electrolytes. When emulsions are required, the active material may be used in the form of self-emulsifying concentrates containing the active material dissolved in the emulsifying agents(s) or in a solvent containing the emulsifying agent(s) compatible with the active material and solvent, a simple addition of water to such concentrates producing compositions ready for use.

The fungicidal compositions according to the invention are particularly useful for disinfecting seed and, more particularly, seed stored in silos. They are advantageously used at the rate of 0.1 to 5 g. of active material per kg. of seed.

In the treatment of leaves or roots of plants, the fungicidal compositions are used at a rate of 10 to 100 g. of active material per hectoliter, 10 hectoliters generally being employed per hectare of area treated.

The following Example illustrates a fungicidal composition according to the invention.

EXAMPLE 25 g of sodium lignosulphite, 470 g. of kaolin and 5 g. of "Tween 80" ("Tween" is a registered Trade Mark) are added to 500 g. of a mixture of equal parts of 1-isopropylcarbamoyl-3-(3,5-dichlorophenyl)hydantoin and of carbendazime. After grinding and sieving, the powder obtained is used, after dilution with water at the rate of 100 g. of powder per 10 liters of water, to protect seed.

Instead of carbendazime any other of the aforementioned fungicides, viz. benomyl, methylthiophanate etc., may be employed to give compositions according to the invention.

I claim:

1. A fungicidal composition which comprises a combination of 1-isopropylcarbamoyl-3-(3,5-dichlorophenyl)hydantoin and another fungicide selected from the class consisting of 2-methoxycarbonylamino-benzimidazole, 1-butyl-carbamoyl-2-methoxycarbonylamino-benzimidazole, and 1,2-bis-(3-methoxycarbonylthioureido)benzene, in association with one or more diluents or adjuvants compatible with the fungicides and suitable for use in agricultural fungicidal compositions, the amount of fungicide in the composition being between 0.005% and 80% by weight of the composition, and the percentage of 1-isopropylcarbamoyl-3-(3,5-dichlorophenyl)hydantoin in the said combination of fungicides present in the composition being between 10% and 90% by weight.

2. The fungicidal composition according to claim 1 in which the percentage of 1-isoproylcarbamoyl-3 -(3,5-dichlorophenyl) hydantoin in the said combination of fungicides present in the composition being between 30% and 70% by weight.

3. The fungicidal composition according to claim 1 which contains a wetting, dispersing or emulsifying agent.

4. The fungidical composition according to claim 3 in which the wetting, dispersing or emulsifying agent is a non-ionic compound.

5. The fungicidal composition according to claim 1 comprising 1-isopropylcarbamoyl-3-(3,5-dichlorophenyl)hydantoin and 2-methoxycarbonylamino-benzimidazole.

6. The fungicidal composition according to claim 1 comprising 1-isopropylcarbamoyl-3-(3,5-dichlorophenyl)hydantoin and 1-butylcarbamoyl-2-methoxycarbonylamino-benzimidazole.

7. The fungicidal composition according to claim 1 comprising 1-isopropylcarbamoyl-3-(3,5-dichlorophenyl)hydantoin and 1,2-bis-(3-methoxycarbonyl-thioureido)-benzene.

* * * * *